United States Patent
Le Grand

(10) Patent No.: US 9,393,228 B2
(45) Date of Patent: Jul. 19, 2016

(54) COMBINATION OF A SLOW SODIUM CURRENT BLOCKER AND A SINUS IF CURRENT INHIBITOR, AND THE PHARMACEUTICAL COMPOSITIONS CONTAINING SAID COMBINATION

(71) Applicant: PIERRE FABRE MEDICAMENT, Boulogne-Billancourt (FR)

(72) Inventor: Bruno Le Grand, Teyssode (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 14/762,184

(22) PCT Filed: Jan. 21, 2014

(86) PCT No.: PCT/EP2014/051106
§ 371 (c)(1),
(2) Date: Jul. 20, 2015

(87) PCT Pub. No.: WO2014/111593
PCT Pub. Date: Jul. 24, 2014

(65) Prior Publication Data
US 2015/0313872 A1    Nov. 5, 2015

(30) Foreign Application Priority Data
Jan. 21, 2013    (FR) ..................... 13 50512

(51) Int. Cl.
*A61K 31/55* (2006.01)
*A61K 31/39* (2006.01)
*A61K 31/00* (2006.01)

(52) U.S. Cl.
CPC ............... *A61K 31/39* (2013.01); *A61K 31/00* (2013.01); *A61K 31/55* (2013.01)

(58) Field of Classification Search
CPC .............................. A61K 31/55; A61K 31/39
USPC ........................................................ 514/212.07
See application file for complete search history.

(56) References Cited

U.S. PATENT DOCUMENTS

| 5,296,482 | A | 3/1994 | Peglion et al. |
| 6,011,032 | A | 1/2000 | Rieu et al. |
| 6,531,469 | B1 | 3/2003 | Rieu et al. |
| 2002/0049229 | A1 | 4/2002 | Yamamoto et al. |

(Continued)

FOREIGN PATENT DOCUMENTS

| CN | 101780091 A | 7/2010 |
| EP | 0184257 A1 | 6/1986 |

(Continued)

OTHER PUBLICATIONS

Tardif, Ivabradine: I(f) inhibition in the management of stable angina pectoris and other cardiovascular diseases, Drugs of Today (Barcelona, Spain: 1998), 2008, 44(3):171-181, 1 page of abstract.*

(Continued)

*Primary Examiner* — T. Victor Oh
(74) *Attorney, Agent, or Firm* — Birch, Stewart, Kolasch & Birch, LLP

(57) ABSTRACT

The present invention relates to the combination of a selective late sodium current blocker and a selective, specific sinus If current inhibitor, and to the pharmaceutical compositions containing said combination.

5 Claims, 1 Drawing Sheet

(56) References Cited

U.S. PATENT DOCUMENTS

2004/0014785 A1 1/2004 Patoiseau et al.
2004/0127552 A1* 7/2004 Vacher ............... C07D 327/02
                                                                                   514/450

FOREIGN PATENT DOCUMENTS

| EP | 0534859 A1 | 3/1993 |
|---|---|---|
| FR | 2822467 A1 | 9/2002 |
| WO | WO 96/12718 A1 | 5/1996 |
| WO | WO 97/05134 A1 | 2/1997 |
| WO | WO 98/38174 A1 | 9/1998 |
| WO | WO 00/43011 A1 | 7/2000 |
| WO | WO 00/73391 A1 | 7/2000 |
| WO | WO 00/61558 A1 | 10/2000 |
| WO | WO 02/081464 A1 | 10/2002 |
| WO | WO 2010/128525 A2 | 11/2010 |

OTHER PUBLICATIONS

"Posters 52: New Drugs," Naunyn-Schmiedeberg's Arch. Pharmacol., vol. 358, Supplement No. 2, 1998, R508.
"Treatment of Disorders of Coronary Arteries and Atherosclerosis," Drug Data Report, vol. 22, No. 9, 2000, p. 790.
Anger et al., "Medicinal Chemistry of Neuronal Voltage-Gated Sodium Channel Blockers," Journal of Medicinal Chemistry, vol. 44, No. 2, Jan. 18, 2001 (Published on web Jan. 11, 2001), pp. 115-137.
Annoura et al., "A Novel Class of Na$^+$ and Ca$^{2+}$ Channel Dual Blockers with Highly Potent Anti-Ischemic Effects," Bioorganic & Medicinal Chemistry Letters, vol. 9, 1999, pp. 2999-3002.
Belardinelli et al., "A Novel, Potent, and Selective Inhibitor of Cardiac Late Sodium Current Suppresses Experimental Arrhythmias," J Pharmacol Exp Ther, vol. 344, Jan. 2013, pp. 23-32.
Belardinelli et al., "Inhibition of the late sodium current as a potential cardioprotective principle: effects of the late sodium current inhibitor ranolazine," Heart, vol. 92, No. 4, 2006, iv6-iv14.
French Search Report dated Sep. 10, 2013, for French Application No. 1350512.
International Search Report dated Mar. 4, 2014, for International Application No. PCT/EP2014/051106.
Le Grand et al., "Sodium Late Current Blockers in Ischemia Reperfusion: Is the Bullet Magic?," J. Med. Chem., vol. 51, No. 13, XP-002673569, 2008 (Published on web Jun. 5, 2008), pp. 3856-3866.
Lètienne et al., "Myocardial protection by F 15845, a persistent sodium current blocker, in an ischemia-reperfusion model in the pig," European Journal of Pharmacology, vol. 624, Available online Sep. 22, 2009, pp. 16-22.
Madge, "Sodium Channels: Recent Developements and Therapeutic Potential," Annual Reports in Medicinal Chemistry, vol. 33, 1998, pp. 51-60.
Okuyama et al., "T-477, a novel Ca$^{2+}$- and Na$^+$ channel blocker, prevents veratridine-induced neuronal injury," European Journal of Pharmacology, vol. 398, 2000, pp. 209-216.
Saint, "Persistent (current) in the face of adversity . . . A new class of cardiac anti-ischaemic compounds on the horizon?," British Journal of Pharmacology, vol. 156, 2009, pp. 211-213.
Shimidzu et al., "Blockade of voltage-sensitive sodium channels by NS-7, a novel neuroprotective compound, in the rat brain," Naunyn-Schmiedeberg's Arch Pharmacol, vol. 355, 1997, pp. 601-608.
Shimojo et al., "Neuroprotective action of a novel compound—M50463—in primary cultured neurons," Brain Research, vol. 815, 1999, pp. 131-139.
Sugiyama et al., "Antiischemic Effects of CP-060S, an Inhibitor of Pathologically Modified Sodium Channels, Assessed in the Canine Experimental Model of Angina Pectoris," Journal of Cardiovascular Pharmacology, vol. 33, No. 1, 1999, pp. 70-77.
Verscheure et al., "Attenuation by R 56865, A Novel Cytoprotective Drug, of Regional Myocardial Ischemia- and Reperfusion-Induced Electrocardiographic Disturbances in Anesthetized Rabbits," Journal of Cardiovascular Pharmacology, vol. 25, 1995, pp. 126-133.

\* cited by examiner

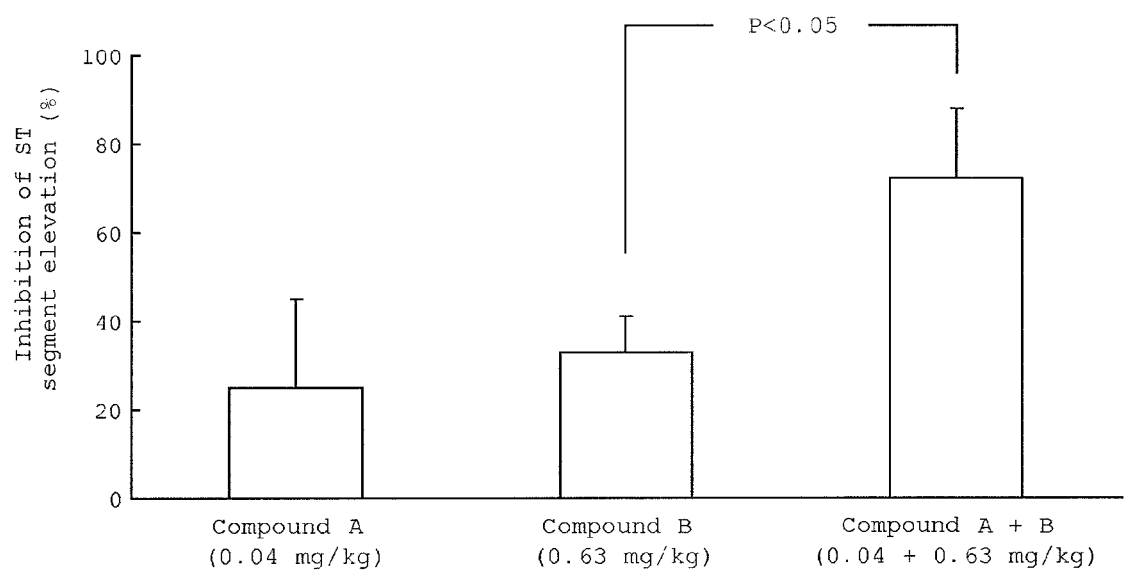

COMBINATION OF A SLOW SODIUM CURRENT BLOCKER AND A SINUS IF CURRENT INHIBITOR, AND THE PHARMACEUTICAL COMPOSITIONS CONTAINING SAID COMBINATION

The present invention relates to the combination of a selective slow sodium current blocker and a selective, specific sinus $I_f$ current inhibitor, and to the pharmaceutical compositions containing said combination.

More particularly, the present invention relates to a combination of a selective slow sodium current blocker, namely 3-(R)-[3-(2-methoxyphenylthio)-2-(S)-methyl-propyl]amino-3,4-dihydro-2H-1,5-benzoxathiepine, or a pharmaceutically acceptable salt thereof, and a selective, specific sinus $I_f$ current inhibitor, or a pharmaceutically acceptable salt thereof.

Preferably, the subject matter of the present invention is a combination of a selective slow sodium current blocker, 3-(R)-[3-(2-methoxyphenylthio)-2-(S)-methyl-propyl]amino-3,4-dihydro-2H-1,5-benzoxathiepine, or a pharmaceutically acceptable salt thereof, and a selective, specific sinus $I_f$ current inhibitor, namely ivabradine, or a pharmaceutically acceptable salt thereof.

Coronary insufficiency, which encompasses various pathologies such as silent ischemia, stable angina, unstable angina, myocardial infarction and heart failure, is one of the leading causes of morbidity and mortality in industrialized nations. The aging of the population should further aggravate this situation in the years to come. In coronary insufficiency, the condition of the contractile function is the principal determinant of the prognosis. However, the attack on the contractile function can be limited only by treatments that preserve the viability of the cardiomyocytes in the region compromised by the ischemia. Two principles make it possible to postpone the death of the cardiac cells exposed to the ischemia and thus to limit the subsequent degree of dysfunction: rapid reoxygenation of tissue and maintenance of the ionic homeostasis of the cells. While, on the one hand, progress in blood clot therapy and in cardiac surgery have had a positive impact, quantifiable in terms of clinical benefits, on the other hand, the contribution made by cytoprotective agents per se is currently virtually nonexistent. Indeed, the medications used in coronary insufficiency—beta-blockers, calcium inhibitors, nitro derivatives, sinus $I_f$ current inhibitors—all act indirectly, principally by a hemodynamic phenomenon. For example, nitro derivatives act by venous and coronary vasodilatation and beta-blockers reduce the heart rate by decreasing the depolarization slope, decrease cardiac work and reduce cardiac oxygen requirements. Calcium inhibitors reduce the tonus of smooth muscles of the peripheral and coronary vessels, the consequence of which is to decrease venous return by easing the work of the left ventricle and to decrease myocardial oxygen consumption, and they improve coronary blood flow by means of their vasodilator action on large arteries. Nicorandil, which is both a nitrate and an ATP-dependent potassium channel activator, is a vasodilator and reduces cardiac work. Trimetazidine has vasodilator effects and acts on energy metabolism of cells exposed to ischemia.

The mechanisms involved in cell death, and those that oppose recovery of cardiac function after reestablishment of blood circulation, are many and complex. Indeed, their relative contributions vary over time and their effects are additive. However, it is accepted that myocardial ischemia disrupts, among other things, the operation of sodium channels and of $Na^+/K^+$ pumps. The latter is the principal mechanism in cardiac cells for expelling $Na^+$ ions. These combined effects are likely involved in the intracellular accumulation of sodium ions observed during ischemia. This intracellular accumulation of sodium ions induces, via the sodium-calcium exchanger, a calcium overload already during the ischemic episode and which is further amplified during the reperfusion process. The excessive rise in intracellular calcium ion concentration reduces contractility and weakens the cytoskeleton. A contraction can result therefrom and lead to cardiac cell death. Furthermore, the contraction of a cell can damage adjacent cells and further extend the necrotic region within the tissue. The change in the contractile function of exposed cardiac cells is reflected overall by a change in cardiac function.

Considering the major role played by sodium overload in the initiation of processes resulting in the death of cardiac myocytes, numerous compounds aimed at preventing it have been disclosed. Two different pathways of sodium ion influx in the cell are the subject of attempts at therapeutic interventions: voltage-dependent sodium channels and sodium-proton exchangers, although the role of the latter during ischemia is disputed.

Voltage-dependent sodium channel blockers have been the subject of extensive research for several decades. Consequently, a large number of compounds are available. They can be divided into three principal subclasses according to their mode of interaction with sodium channels.

The first subclass groups together class I antiarrhythmics, local anesthetics and certain anticonvulsants, such as, for example, lidocaine, flecainide, phenytoin and quinidine, which have a common interaction site at cardiac and neuronal sodium channels. These agents have little or no cardiac cytoprotective activity. Moreover, their use in the treatment of coronary diseases has a high risk of side effects. Indeed, it has been shown clinically that compounds such as flecainide and encainide have a high arrhythmogenic potential when the electrophysiological conditions are changed, such as, for example, during ischemia.

The second subclass comprises neuronal sodium channel blockers or modulators that do not appear to significantly affect cardiac voltage-dependent sodium channels. Compounds belonging to this subclass are principally claimed for the treatment of central and/or peripheral nervous system diseases and disorders.

This subclass groups together compounds of various chemical classes (Annual Reports in Medicinal Chemistry 1998, 33, 51; J. Med. Chem. 2001, 44, 115), M50463 (Brain Research, 1999, 815, 131), NS-7 (Naunyn-Schmiedeberg's Arch. Pharmacol, 1997, 355, 601), T-477 (European J. Pharmacol, 2000, 398, 209), certain derivatives of arylpiperidines (Bioorg. Med. Chem. Lett., 1999, 9, 2999), of piperidinols (WO 00/61558), of pyrazines (WO 98/38174), of aromatic aryl-heterocycles (WO 00/57877).

The advantage of these derivatives as cardiac cytoprotective agents appears to be limited.

The third subclass comprises compounds that act at cardiac sodium channels but via a different mechanism from that of class I antiarrhythmic agents. These agents block the non-inactivated sodium channel and thus reduce the slow inactivation component of the sodium current. A single gene (SCN5A) encodes the human cardiac sodium channel Nav1.5. This channel is responsible for the fast and sustained components of the sodium current. Several $Na_v1.5$ blockers have been disclosed, such as the derivative R 56865, originally developed as an anti-hypoxic/anti-anoxic agent (EP 0184257). The protective activity of ranolazine (Belardinelli et al., Heart, 2006, 92, Suppl 4, iv6-iv14), marketed as an antianginal, was only belatedly revealed to be via $Na_v1.5$ blocking. GS-967 has been claimed as a powerful selective slow sodium current inhibitor (Belardinelli et al., J. Pharmacol. Exp. Ther. 2013, 344, 23). Other derivatives, claimed, among other things, as cardiac cytoprotective agents, may belong to this class. That is the case, for example, of the derivative CRE-319M2 (Naunyn-Schmiedeberg's Arch. Pharmacol. 1998, 358, suppl. 2, 508), 1-cis-diltiazem (European Journal Pharmacology, 1998, 358, 554), CP-060S (Journal Cardiovascular Pharmacology, 1999, 33, 70), ST-6 (Drug Data Report 2000, 22, 790), the benzofurans disclosed in the international application WO 96/12718, the benzo(thia/oxa)zines disclosed in the international applications WO 97/05134 and WO 00/43391, and the aryl-isothioureas disclosed in the international application WO 00/43011.

3-(R)-[3-(2-Methoxyphenylthio)-2-(S)-methyl-propyl]amino-3,4-dihydro-2H-1,5-benzoxathiepine is a selective slow sodium current blocker. This compound is disclosed in the patent EP 1370547.

The Inventors discovered that, surprisingly, a selective slow sodium current blocker, more particularly 3-(R)-[3-(2-methoxyphenylthio)-2-(S)-methyl-propyl]amino-3,4-dihydro-2H-1,5-benzoxathiepine, combined with a selective, specific sinus $I_f$ current inhibitor, had significant anti-ischemic activity. This protective activity is related to synergy between the active ingredients.

The selective slow sodium current inhibitors in the combination according to the invention are more particularly 3-(R)-[3-(2-methoxyphenylthio)-2-(S)-methyl-propyl]amino-3,4-dihydro-2H-1,5-benzoxathiepine, ranolazine and (6-[4-(trifluoromethoxy)phenyl]-3-(trifluoromethyl)-[1,2,4]triazolo[4,3-a]pyridine) (GS-967), or a pharmaceutically acceptable salt thereof.

The selective, specific sinus $I_f$ current inhibitors, and more particularly ivabradine or a pharmaceutically acceptable salt thereof, and more particularly the hydrochloride thereof, have highly advantageous pharmacological and therapeutic properties, in particular negative chronotropic properties (reduction of heart rate), which makes these compounds useful in the treatment or prevention of various clinical presentations of myocardial ischemia such as angina pectoris, myocardial infarction and associated arrhythmias, as well as various pathologies involving arrhythmias, in particular supraventricular arrhythmias, and in heart failure.

The selective, specific sinus $I_f$ current inhibitors in the combination according to the invention are more particularly ivabradine, zatebradine, cilobradine and (−)-N-{2-[(R)-3-(6,7-dimethoxy-1,2,3,4-tetrahydroisoquinoline-2-carbonyl)piperidino] ethyl}-4-fluorobenzamide (YM-758), or a pharmaceutically acceptable salt thereof.

The preparation and the therapeutic use of ivabradine and of the additive salts thereof with a pharmaceutically acceptable acid, more particularly the hydrochloride thereof, were disclosed in the European patent EP 05340859.

The subject matter of the present invention is, therefore, the combination of a selective slow sodium current blocker and a selective, specific sinus $I_f$ current inhibitor.

Another subject matter of the invention concerns 3-(R)-[3-(2-methoxyphenylthio)-2-(S)-methyl-propyl]amino-3,4-dihydro-2H-1,5-benzoxathiepine, or a pharmaceutically acceptable salt thereof, as a selective slow sodium current blocker combined with a selective, specific sinus $I_f$ current inhibitor.

The present invention also relates to the combination of a selective slow sodium current blocker and ivabradine, or a pharmaceutically acceptable salt thereof, as a selective, specific sinus $I_f$ current inhibitor.

Another preferred embodiment of the invention consists of the combination of 3-(R)-[3-(2-methoxyphenylthio)-2-(S)-methyl-propyl]amino-3,4-dihydro-2H-1,5-benzoxathiepine, or a pharmaceutically acceptable salt thereof, as a selective slow sodium current blocker and ivabradine, or a pharmaceutically acceptable salt thereof, as a selective, specific sinus $I_f$ current inhibitor.

In the present invention, angina (or angor) pectoris is a myocardial ischemia which manifests itself as chest pain resulting from a lack of myocardial oxygen supply. Most often this lack of oxygen is secondary to reduced blood flow in a coronary artery caused, for example, by the formation of a plaque of atheroma which reduces the artery's diameter. The result is a discrepancy between the oxygen demands of the myocardium and the oxygen supply provided by coronary circulation. Angina pectoris is referred to as "stable" if the pain is not new, it occurs under familiar circumstances, and there is no recent worsening. Angina pectoris is referred to as "unstable" if the pain recently appeared, or has become more frequent, or appears under different circumstances than before. Unstable angina falls within the scope of acute coronary syndrome and requires emergency hospitalization.

This discrepancy between oxygen needs and supply is all the greater during physical exertion requiring more oxygen. Typically, ischemia during angina is short in duration and is reversible, with no cell destruction. It is prolonged and is responsible for significant cell destruction during myocardial infarction. Cardiac ischemia (with or without angina pectoris) may be present without coronary atheroma. That is the case, for example, with Prinzmetal's angina where coronary arteries suddenly contract due to a generally transient spasm. That is the case also with hypertrophic cardiomyopathies where the normal coronary system is insufficient to provide adequate oxygenation to a muscle with a much larger volume and a greater oxygen demand. Transient myocardial ischemia may not be associated with pain, in which case it is referred to as silent ischemia. It may manifest itself by a change in the contraction of one or more cardiac walls (visualized, for example, during a stress echocardiography) and by disruptions of electrical activity (visualized with an electrocardiogram during an exercise test).

In the present invention, heart failure is clinically defined as "a state in which the heart is no longer able to sufficiently perfuse the peripheral organs at rest and under stress." It can be objectified or not through the ventricular ejection fraction or the left ventricular ejection fraction defined as the ratio between the end-systolic volume and the end-diastolic volume.

Heart failure due to systolic dysfunction of the left ventricle is not the only form of heart failure. Increasingly often, patients with heart failure have an ejection fraction greater than 40%. The proportion of heart failure referred to as "diastolic heart failure" or "heart failure with preserved systolic function" increases with age. It currently accounts for 30% to 40% of hospitalizations for heart failure and, after the age of 80, its frequency exceeds that of heart failure due to systolic dysfunction. Diastolic heart failures generally feature both prolonged ventricular relaxation and a reduction in the distensibility of the left ventricle chamber. The basic causes are ischemic, hypertensive and elderly-patient cardiopathies. Predisposing factors are age, sex (women), diabetes, obesity and arterial hypertension. Concentric remodeling of the left ventricle, with or without hypertrophy, consistently gives rise to disruption of diastolic function. In most cases a triggering factor is found to be the cause of a congestive attack. The frequency of "diastolic" heart failure increases with age. No treatment has hitherto demonstrated efficacy in this pathology, the mortality of which (50% at 4 years) corresponds to that of systolic heart failure.

In the present invention, by "pharmaceutically acceptable" is meant that which is useful in the preparation of a pharmaceutical composition that is generally safe, nontoxic and neither biologically nor otherwise undesirable and that is acceptable for veterinary use as well as human pharmaceutical use.

By "pharmaceutically acceptable salts" of a compound is meant salts that are pharmaceutically acceptable, as defined herein, and that have the desired pharmacological activity of the parent compound. Such salts comprise:

acid addition salts formed with inorganic acids such as hydrochloric acid, hydrobromic acid, sulfuric acid, nitric acid, phosphoric acid and the like, or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and the like; or salts formed when an acid proton present in the parent compound either is replaced by a metal ion, for example an alkaline metal ion, an alkaline-earth metal ion or an aluminum ion; or coordinates with an organic or inorganic base. Acceptable organic bases comprise diethanolamine, ethanolamine, N-methylglucamine, triethanolamine, tromethamine and the like. Acceptable inorganic bases comprise aluminum hydroxide, calcium hydroxide, potassium hydroxide, sodium carbonate and sodium hydroxide.

It should be understood for this present invention that all references to pharmaceutically acceptable salts comprise the solvent addition forms (solvates) or crystalline forms (polymorphs) as defined herein, of the same acid addition salt.

The present invention further relates to a pharmaceutical composition comprising as active ingredients a selective slow sodium current blocker, or a pharmaceutically acceptable salt thereof, and a selective, specific sinus $I_f$ current inhibitor and at least one pharmaceutically acceptable excipient.

Advantageously, the pharmaceutical composition comprises as active ingredients 3-(R)-[3-(2-methoxyphenylthio)-2-(S)-methyl-propyl]amino-3,4-dihydro-2H-1,5-benzoxathiepine, or a pharmaceutically acceptable salt thereof, and a sinus $I_f$ current inhibitor, or a pharmaceutically acceptable salt thereof, and at least one pharmaceutically acceptable excipient.

In another advantageous manner, the pharmaceutical composition comprises as active ingredients a selective slow sodium current blocker, or a pharmaceutically acceptable salt thereof, and ivabradine, or a pharmaceutically acceptable salt thereof, and at least one pharmaceutically acceptable excipient.

In an even more advantageous manner, the pharmaceutical composition according to the invention comprises as active ingredients 3-(R)-[3-(2-methoxyphenylthio)-2-(S)-methyl-propyl]amino-3,4-dihydro-2H-1,5-benzoxathiepine, or a pharmaceutically acceptable salt thereof, and ivabradine, or a pharmaceutically acceptable salt thereof, and at least one pharmaceutically acceptable excipient.

In a still more advantageous manner, the pharmaceutical composition according to the invention comprises as active ingredients 3-(R)-[3-(2-methoxyphenylthio)-2-(S)-methyl-propyl]amino-3,4-dihydro-2H-1,5-benzoxathiepine, or a pharmaceutically acceptable salt thereof, and ivabradine in hydrochloride form, and at least one pharmaceutically acceptable excipient.

The pharmaceutical composition according to the present invention is for use in the treatment of angina pectoris, ischemia and/or heart failure.

The pharmaceutical composition according to the present invention is more particularly for use in the treatment of heart failure with preserved systolic function.

The pharmaceutical composition according to the present invention may be administered orally or via any other pharmaceutical route of administration.

The pharmaceutical compositions according to the present invention may be formulated for administration to mammals, including humans. These compositions are designed to be able to be administered orally, sublingually, subcutaneously, intramuscularly, intravenously, transdermally, locally or rectally. In this case, the active ingredients may be administered in unit dose administration forms, in a mixture with conventional pharmaceutical carriers, to animals or to human beings. Suitable unit dose administration forms comprise oral forms such as tablets, capsules, powders, granules and oral solutions or suspensions, sublingual and buccal administration forms, subcutaneous, topical, intramuscular, intravenous, intranasal or intraocular administration forms, and rectal administration forms.

When a solid composition in tablet form is prepared, the principal active ingredients are mixed with a pharmaceutical carrier such as gelatin, starch, lactose, magnesium stearate, talc, gum arabic, silica or analogues. The tablets may be coated with sucrose or other suitable materials or they may be treated such that they have extended or delayed activity and that they continuously release a predetermined amount of active ingredient.

A capsule preparation is obtained by mixing the active ingredients with a diluent (optional step) and pouring the mixture obtained into soft or hard capsules. Examples of diluents include lactose, dextrose, sucrose, mannitol, sorbitol, cellulose and glycerin.

A preparation in syrup or elixir form may contain the active ingredients along with a sweetener, an antiseptic, as well as a flavor enhancer and a suitable colorant.

Water-dispersible powders or granules may contain the active ingredients in a mixture with dispersants or wetting agents, or suspending agents, just as with flavor enhancers or sweeteners.

For rectal administration use is made of suppositories, which are prepared with binders that melt at rectal temperature, for example cocoa butter or polyethylenes glycols.

For parenteral (intravenous, intramuscular, etc.), intranasal or intraocular administration, use is made of aqueous suspensions, isotonic saline solutions or sterile injectable solutions containing pharmacologically compatible dispersants and/or wetting agents.

The active ingredients may be formulated also as microcapsules, optionally with one or more additional carriers.

Advantageously, the pharmaceutical composition according to the present invention is for oral or intravenous administration, more advantageously for oral administration.

The dosages of the pharmaceutical compositions comprising a slow sodium current blocker and a selective, specific sinus $I_f$ current inhibitor in the compositions of the invention are adjusted in order to obtain the desired therapeutic response for a composition specific to the method of administration. The selected dosage level thus depends on the desired therapeutic effect, the chosen administration route, the desired duration of treatment, the patient's weight, age and sex, and the sensitivity of the individual to be treated. Consequently, the optimal dosing regimen should be determined as a function of the parameters considered to be relevant by the skilled person. Preferentially, 3-(R)-[3-(2-methoxyphenylthio)-2-(S)-methyl-propyl]amino-3,4-dihydro-2H-1,5-benzoxathiepine, or a pharmaceutically acceptable salt thereof, is administered in acceptable pharmaceutical compositions where the daily dose is between 0.1 and 100 mg per day, more preferentially the daily dose is between 0.5 and 10 mg per day, and still more preferably from 2.5 to 60 mg per day.

The daily dose of the selective, specific sinus $I_f$ current inhibitor, in particular ivabradine, may vary from 2.5 to 30 mg per day, more preferentially from 10 to 15 mg per day, and still more preferably from 5 to 15 mg per day. The dose of the selective, specific sinus $I_f$ current inhibitor may be less than that used when it is administered alone.

The following example illustrates the invention without limiting the its scope.

Pharmacological Test:

The anti-ischemic activity of 3-(R)-[3-(2-methoxyphenylthio)-2-(S)-methyl-propyl]amino-3,4-dihydro-2H-1,5-benzoxathiepine combined with ivabradine was evaluated in a model of ST segment elevation by occlusion of the circumflex coronary artery in anesthetized rabbits.

Methods:

Male rabbits (2.2-2.5 kg) are anesthetized with pentobarbital. A catheter is placed in a carotid artery in order to continuously measure the animal's blood pressure. Blood samples are taken in order to regularly check blood gases and to modify ventilation parameters as needed. The compounds to be tested or the carriers are administered via a catheter placed in an ear vein. An electrocardiogram is recorded, also continuously, in configuration II in order to determine the variations of amplitude of the ST segment. The animal's thorax is opened and a ligature is placed around the left coronary artery (circumflex) in order to induce regional myocardial ischemia (Verscheure et al., 1995). After a period of stabilization of all hemodynamic parameters, the compounds are administered in a slow bolus (1 minute). Five minutes after the compounds are administered, the circumflex artery is occluded for 5 minutes and then the ligature is released. The heart is removed and the risk area (ligatured region of the circumflex artery) is evaluated. Four groups of rabbits are studied:

group receiving carrier: 40% polyethylene 300, 60% physiological saline;
group receiving 3-(R)-[3-(2-methoxyphenylthio)-2-(S)-methyl-propyl]amino-3,4-dihydro-2H-1,5-benzoxathiepine (compound A) at a dose of 0.04 mg/kg;
group receiving ivabradine hydrochloride (compound B) at a dose of 0.63 mg/kg;
group receiving compound A (0.04 mg/kg)+compound B (0.63 mg/kg).

The doses were selected in order to have submaximal pharmacological activities and thus to uncover potential additive or synergistic effects.

Results

Occlusion of the left coronary artery causes elevation of the ST segment; this amplitude variation reaches 0.33±0.04 mV under the control conditions (that is, with the carrier). Compound A causes a slight inhibition of this ST segment elevation, without changing heart rate or blood pressure (Table 1). Compound B also induces a lower ST segment elevation (see the figure) but induces a relatively significant and constant bradycardia. Surprisingly, the combination of compounds A and B causes a very large reduction of ST segment elevation (inhibition above 70%) and this reduction is very statistically significant ($p<0.001$ versus the carrier group, $p<0.05$ versus the compound B group). The variations of heart rate induced by the combination of compounds A and B are similar to those induced by compound B administered alone.

The figure summarizes these results: it represents the inhibition of ST segment elevation by compound A, compound B and the combination of the two compounds. Table 1 shows the mean blood pressure values and heart rate values measured 5 minutes after administration of the various compounds:

TABLE 1

| Compounds | Mean blood pressure (mmHg) | | Heart rate (bpm) | |
|---|---|---|---|---|
| Carrier | 84 ± 3 | | 264 ± 8 | |
| Compound A | 92 ± 4 | p = NS | 275 ± 10 | p = NS |
| Compound B | 92 ± 3 | p = NS | 211 ± 10 | p < 0.001 |
| Compound A + B | 85 ± 5 | p = NS | 205 ± 4 | p < 0.001 |

These experiments show that, in a model of cardiac ischemia, the combination of a slow sodium current blocker and a sinus $I_f$ current inhibitor provides myocardial protection that is much superior to that obtained with one or the other of these two treatments used alone (see the figure). On the other hand, this combination does not induce additional effects on hemodynamic parameters as shown in Table 1 above.

The invention claimed is:

1. A combination of 3-(R)-[3-(2-methoxyphenylthio)-2-(S)-methyl-propyl]amino-3,4-dihydro-2H-1,5-benzoxathiepine, or a pharmaceutically acceptable salt thereof, and ivabradine, or a pharmaceutically acceptable salt thereof.

2. The combination according to claim 1, characterized in that ivabradine is in hydrochloride form.

3. A pharmaceutical composition comprising as active ingredient a combination according to claim 1 alone or in combination with at least one pharmaceutically acceptable excipient.

4. A method of treating angina pectoris, ischemia and/or heart failure which comprises administering to a patient in need thereof an effective amount of the composition according to claim 3.

5. The method according to claim 4 wherein said heart failure is heart failure with preserved systolic function.

* * * * *